United States Patent
Cesarczyk

[11] Patent Number: 5,891,074
[45] Date of Patent: *Apr. 6, 1999

[54] PRESSURE WOUND DRESSING

[75] Inventor: Edward J. Cesarczyk, North Easton, Mass.

[73] Assignee: Avitar, Inc., Canton, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 697,327

[22] Filed: Aug. 22, 1996

[51] Int. Cl.⁶ .................................................. A61F 13/00
[52] U.S. Cl. ........................... 602/42; 602/53; 128/109.1
[58] Field of Search .................................. 602/41, 53, 42, 602/64–66; 128/101.1, 108.1, 109.1

[56] References Cited

U.S. PATENT DOCUMENTS

| | | | |
|---|---|---|---|
| 551,237 | 12/1895 | Stewart | 128/106.1 |
| 566,738 | 9/1896 | Brickner et al. | 128/106.1 |
| 3,490,448 | 1/1970 | Grubb | 602/53 |
| 3,954,109 | 5/1976 | Patel | 602/53 |
| 4,005,709 | 2/1977 | Laerdal | 602/53 |
| 4,224,945 | 9/1980 | Cohen | 602/53 |
| 4,377,159 | 3/1983 | Hansen | 602/53 |
| 5,209,718 | 5/1993 | McDaniel | 602/41 |
| 5,690,610 | 11/1997 | Ito et al. | 602/53 |

FOREIGN PATENT DOCUMENTS 330373  8/1989  European Pat. Off. ................. 602/53

*Primary Examiner*—Mark O. Polutta
*Attorney, Agent, or Firm*—George W. Neuner

[57] ABSTRACT

A pressure wound dressing has a flexible support layer, a pressure exerting support member attached to and extending from one side of the flexible support layer and, preferably, a layer of pliant absorbent material attached to the pressure exerting support member. The flexible support layer has an adhesive layer on the side from which the support member extends. Preferably, a removable liner is positioned on the adhesive layer opposite to the support layer. The pressure exerting support member preferably is formed from a sheet of material to provide two surfaces oriented at an angle with respect to each other.

32 Claims, 4 Drawing Sheets

PRESSURE WOUND DRESSING

INTRODUCTION

The present invention relates to a pressure bandage or wound dressing, particularly to a pressure dressing having structure to exert pressure on a wound to stop or control bleeding.

BACKGROUND OF THE INVENTION

Presently, in order to stop bleeding wounds, for example when an artery is bleeding, pressure is typically applied externally by manual exertion of pressure for a period of time sufficient to control or stop the bleeding. Unless the patient is able to provide the pressure, this method for controlling bleeding can be time consuming and somewhat cumbersome for the clinician administering the procedure as well as discomforting for the patient due to inadvertent changes in the pressure applied manually. As such, this procedure also can be costly due to the requirement for a person to exert the pressure.

It is therefore desirable to provide a wound dressing to apply a controlled pressure to a patient. Such a pressure wound dressing lessens the discomfort to the patient, avoids the requirement for personal administration of pressure, and can reduce the cost of providing health care. Such a device would be expedient and convenient to apply, and would minimize patient discomfort.

BRIEF SUMMARY OF INVENTION

The pressure wound dressing of the present invention comprises a flexible support layer, a pressure exerting support member attached to and extending from the support layer and, preferably, a layer of a pliant absorbent material attached to the pressure exerting support member. The layer of pliant absorbent material is attached to a first surface of the pressure exerting support member and a second surface is attached to the support layer. The support layer has an adhesive layer for attachment to the skin of a patient, which closes the surfaces of the pressure exerting member, thereby exerting a pressure on the wound. Preferably, an adhesive liner is removably attached to the adhesive layer. The pressure wound dressing is configured, as required, to cover various wounds in various locations on a patient.

The pressure exerting support member preferably comprises a sheet of fold resistant material configured with a fold to divide the sheet into two portions at an angle with each other wherein, when the two portions are moved together, the material exerts a force to return the portions to their original position. An external surface of one of the portions of the fold resistant material is attached to the pliant support member. The external surface of the other portion of the fold resistant material is covered with the pliant absorbent material for contact with the wound. Typically, the pressure exerting support member is positioned in the center of the pliant support member so that the adhesive layer of the pliant support member firmly attaches the wound dressing structure to the patient's skin.

The adhesive liner of the pressure wound dressing is conveniently provided in two portions, e.g., creating two halves of the liner, thereby allowing the pressure exerting support member in the center portion of the pliant support member to extend out of the plane of the adhesive layer while covering the exposed adhesive layer with the liner. Thus, an opening is located in the center of the adhesive liner to accommodate the pressure exerting support member and attached pliant absorbent material.

The pressure wound dressing is typically packaged in a sterile wrapper. When the pressure wound dressing is removed from its sterile package, the pliant absorbent material layer is placed against the wound and the opposite portion of the pressure exerting support member (attached to the pliant support member) is pushed to close the fold resistant material and place the two portions in contact. The adhesive liner is then removed and the adhesive side of the pliant support member is attached to the skin of the patient. When the pressure wound dressing is thus positioned, the force exerted by the fold resistant material to return to its original position maintains a controlled force on the wound to control or stop bleeding.

DETAILED DESCRIPTION OF THE INVENTION INCLUDING PREFERRED EMBODIMENTS

Figure 1:
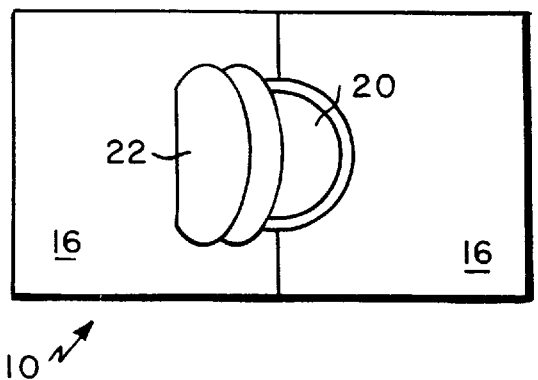
FIG. 1 is a top view of a pressure wound dressing in accord with a preferred embodiment of the present invention.
Figure 2:
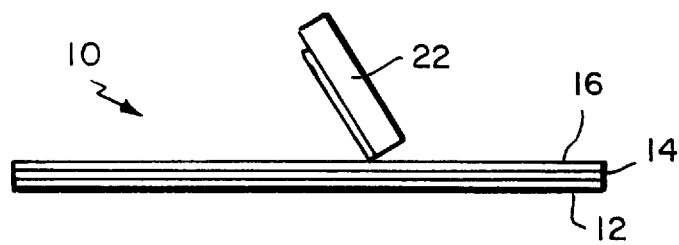
FIG. 2 is a front elevational view of the pressure wound dressing shown in FIG. 1.
Figure 3:
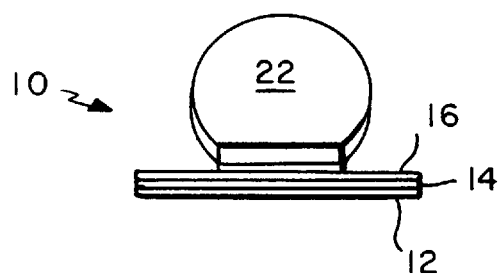
FIG. 3 is a side view of the pressure wound dressing of FIG. 1.
Figure 4:
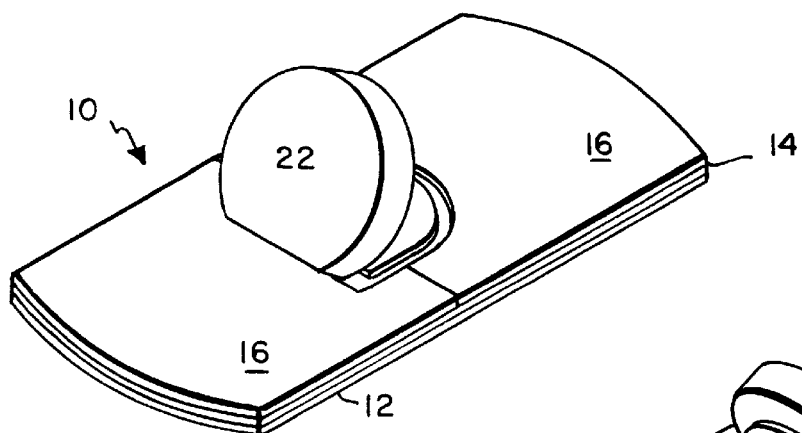
FIG. 4 is an isometric view of the device of FIG. 1.
Figure 5:
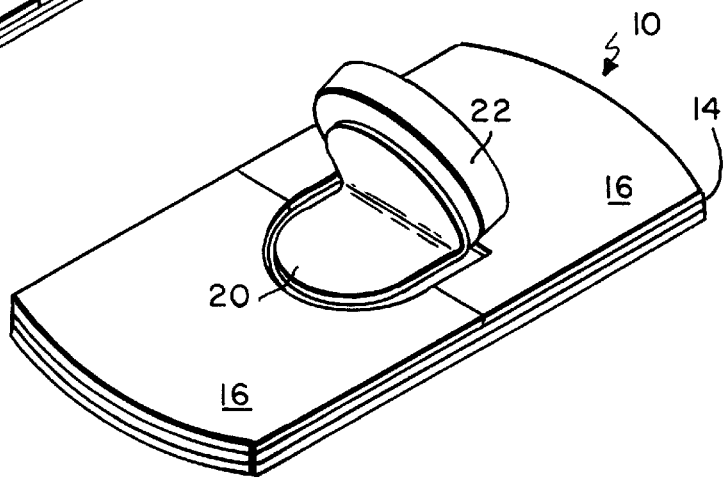
FIG. 5 is another isometric view from a reverse angle of the device of FIG. 1.

With reference to the drawings (FIGS. 1–6), one embodiment of a pressure wound dressing 10 comprises a flexible support layer 12 with an adhesive layer 14 and a adhesive liner 16. Attached to the flexible support layer 12 is a pressure exerting support member 20 to which is attached a layer 22 of a pliant absorbent material. The adhesive layer 14 is applied to the flexible support layer and the adhesive liner 16 is preferably attached to the adhesive layer in two pieces (see FIG. 1).

The flexible support layer is preferably made of a material that will provide sufficient strength to resist the force exerted by the pressure exerting support member. The material should also be pliant or flexible to conform to the patient. Examples of suitable materials include films of polyvinylchloride, polyethylene, polyurethane, ethylvinylacetate and polyethylene/ethylvinylacetate. Other materials known to those skilled in the art can also be used.

The pressure exerting support member 20 is made preferably of plastic material formed in a folded position with an angle between the folded portions preferably less than about 90°, more preferably at least about 45°. A preferred range of angles is from about 50° to about 75°. The material should be fold resistant. In other words when folded to have an angle of 0°, i.e. the folded sides in contact, the material will exert a force to return to its originally formed shape. Thus, when the pressure holding the folded sides in contact is released, the material returns substantially to its originally formed shape. Examples of suitable materials include polycarbonate, polyethylene, polyurethane, spring steel, and the like. The folded material should be of a thickness to provide a pressure of at least about 5 oz. per square inch (psi) when tested in accord with the procedure described below. Generally, it is desired that the pressure does not exceed about 150 oz. psi. Preferably, the folded material should provide a pressure of at least 35 oz. psi. The maximum pressure exerted by the folded material is limited by the adhesive used for applying the wound dressing to the patient.

The pressure exerted by the pressure exerting support member is determined as follows. Testing was conducted on a Chatillon Force Measurement device (Model #UTSE-2) that was equipped with a compression sensor, compression plate, ram platform, console and printer. The samples were configured the same as a pressure exerting support member for a pressure dressing in accord with the present invention.

Figure 6:
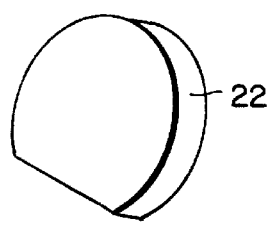
FIG. 6 illustrates an exploded view of components of a pressure wound dressing in accord with an embodiment of the present invention.
Figure 6:
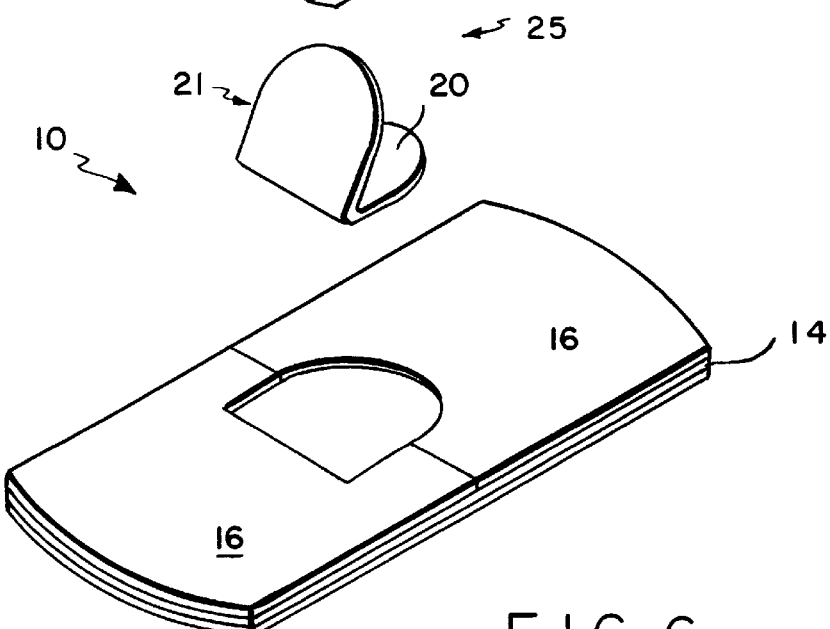

For example, clear polycarbonate plastic sheets having a thickness from 0.015 inch to 0.030 inch were fabricated into pressure exerting support members by creating a fold in the center to provide two opposing surfaces that included a rectangular area 0.625×0.625 inches and a full radius on the distal end as shown in FIG. 6. The angle between the surfaces of support member 20 was 60°.

All tests were conducted in accord with the general compression testing instructions for the Chatillon device. Each test sample was positioned in the center of the ram platform with one surface of the support member secured to the platform (e.g., with adhesive) to prevent pivoting. Prior to positioning the test sample, a 0.125 inch datum point was established between the compression plate and the ram platform using standard calipers. The maximum thickness of a fully collapsed support member was approximately 0.062 inch thick which, therefore, allowed approximately 0.062 inch clearance tolerance to prevent potential damage to the test sample or testing device. After attaching the sample to the ram plate, the ram was raised until the uppermost portion of the test sample was in contact with the compression plate. A tare pressure of 0.05 pounds was established, the console was set to zero and the "maximum hold" control was engaged.

The tests were conducted with the ram platform speed set at 2 inches per minute and completed when the ram platform stopped at the preset 0.125 inch (tolerance—+0.010, −0.000) distance from the compression plate. Upon completion of a run, the test data was printed by the console printer and, based on the surface area of the pressure exerting support member, the data was converted into ounces per square inch (oz. psi or $oz/in^2$).

Preferred pressure wound dressings incorporate a pliant absorbent material attached to the pressure exerting support member. The pliant absorbent material layer 22 preferably comprises a pliant material, more preferably a resilient material such as a foamed polymeric material, having a preferred dry thickness of about 0.002 inch to about 0.375 inch, more preferably about 0.062 inch to about 0.187 inch. Conveniently, the absorbent layer is approximately 0.125 inch (⅛ inch) thick in the embodiment illustrated in FIGS. 1–5. As is readily apparent to the skilled artisan, the thickness can vary depending upon particular applications. Absorbent materials can be selected from, for example, open or closed cell polyethylene foam, open or closed cell polyurethane foam, polyvinylchloride foam, spun-laced polyester, rubber, cotton, gauze, cellulose fiber, or the like. Examples of materials preferred for the absorbent layer are HYDRASORB® open cell polyurethane foam produced by Avitar, Inc., Canton, Mass. or cellulose fiber.

However, the pressure wound dressing can be made without a pliant absorbent material layer. An absorbent layer can be added by the clinician by placing it over the wound before applying the pressure wound dressing. Also, in some cases it is desirable to use a layer of collagen or other hemostatic material in place of the pliant absorbent material, or as an additional layer in combination with the pliant absorbent material. In such cases where the collagen or other hemostatic layer is used with the pliant absorbent layer, the hemostatic layer is placed in contact with the wound surface.

Typically, the area covered by the pliant absorbent material layer will from about 150% to about 300% of the area of the wound or about eight times (8×) the area of a puncture site (e.g., of a catheter). However, the area will depend upon the type of wound for which the pressure wound dressing is designed as is well understood by those skilled in the art.

The adhesive layer can be a liquid, paste or double sided tape applied to the support. It is preferred that the adhesive be of a non-sensitizing type adhesive such as, for example, hypoallergenic, pressure sensitive, acrylate adhesive. Preferably the adhesive has a peel strength (adhesion to steel) of at least about 10 oz/in. to about 60 oz/in., more preferably at least about 35 oz/in. to about 45 oz/in. Preferably, the adhesive has a minimum 180 degree peel strength of about 40 oz/in. It is further advantageous that the adhesive have, moisture absorbing, anti-bacterial and/or anti-fungal properties to help reduce the possibility of infection at the wound site.

The liner can be made of a plastic or plastic-like substance such as, for example, a siliconized polycoated Kraft release paper or Teflon-coated paper. The liner should be easily removable from the adhesive, being pealed therefrom with little force on the part of the clinician, thereby minimizing the possibility of jarring or moving the catheter when fastening to a patient.

Manufacturing of the pressure wound dressing can be accomplished by assembling the appropriate layers and utilizing a standard die-cutting technique known in the industry to form an adhesive coated flexible support having the adhesive liner as illustrated by reference number 25 in FIG. 6. The pressure exerting support member 20 is formed with its preset angle by heat and pressure deforming of a sheet of the material and annealing the formed member to relieve stresses. The pressure exerting support member is adhered to the flexible support member 12 and pliant absorbent material layer 22 is adhered to surface 21. The pressure wound dressing is then wrapped and sterilized by conventional techniques. Those skilled in the art will recognize other suitable materials and means of manufacturing the pressure wound dressing.

Figure 7:
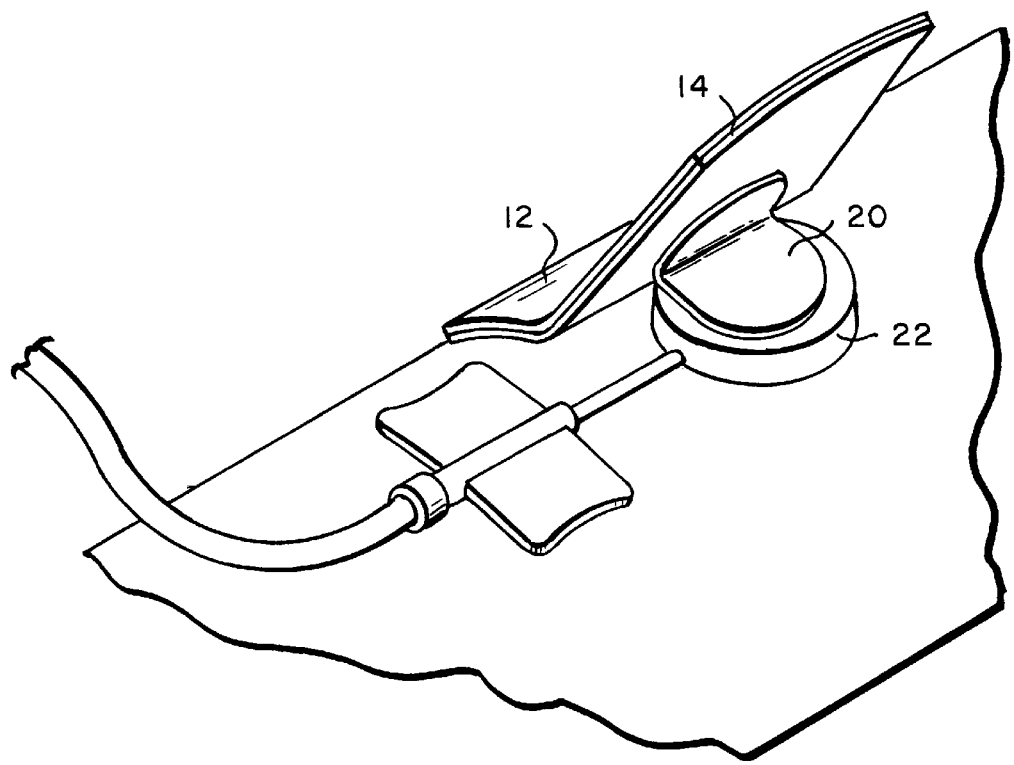
FIG. 7 illustrates a pressure wound dressing in accord with the invention being applied over a catheter inserted into the arm of a patient.
Figure 8:
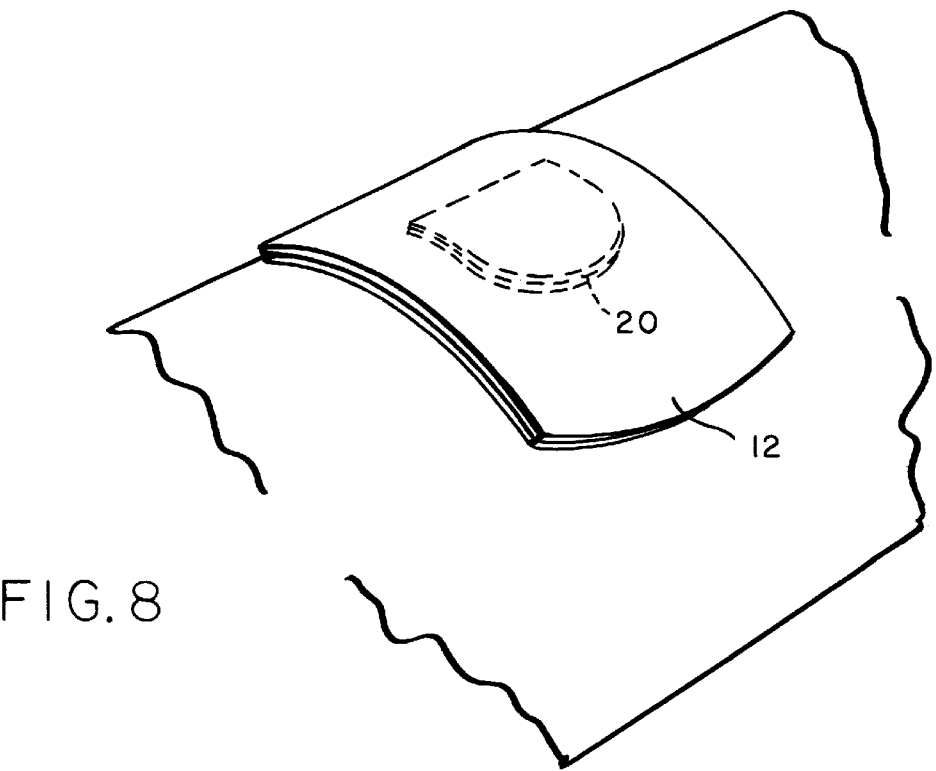
FIG. 8 illustrates a pressure wound dressing of the invention covering a wound on a limb of a patient.
Figure 9A:
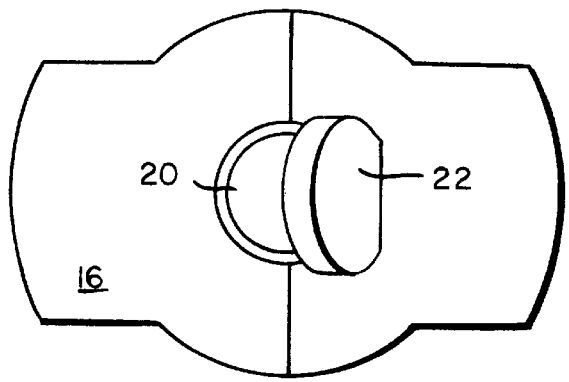
FIGS. 9A–9D illustrate alternative shapes for pressure wound dressings in accord with the invention.
Figure 9B:
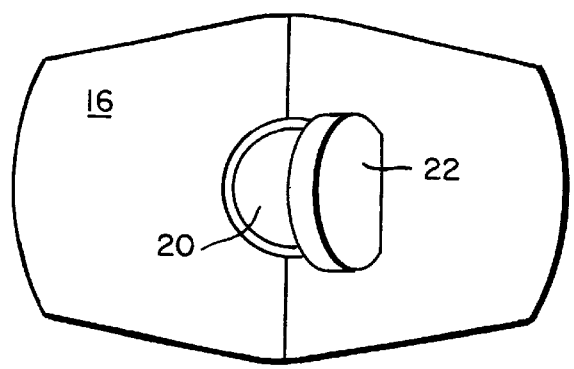
Figure 9C:
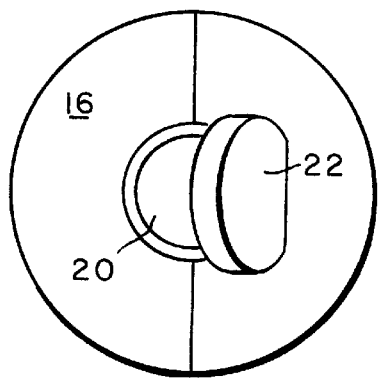
Figure 9D:
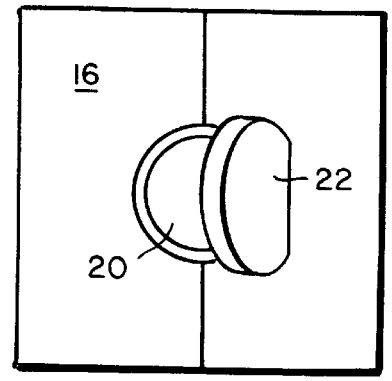

In use, as illustrated in FIG. 7, the adhesive liner is removed and the pliant absorbent material layer 22 is placed against the wound. The opposite portion of the pressure exerting support member (attached to the pliant support member 12) is pushed to close the fold resistant material and place the two portions in contact. The adhesive side of the pliant support member is attached firmly to the skin of the patient around the pressure exerting support member. When the pressure wound dressing is thus positioned, the force exerted by the fold resistant material to return to its original position maintains a controlled force on the wound to control or stop bleeding.

Although the invention has been described in detail with reference to the preferred embodiments thereof, it will be appreciated by those skilled in the art, upon considering the present specification and drawings, that modifications and/or improvements may be made within the spirit and scope of the invention. For example, other spring like mechanisms could be used by those skilled in the art to make the pressure exerting support member.

I claim:

1. A pressure wound dressing comprising a flexible support layer, and a pressure exerting support member attached to and extending from one side of the flexible support layer, wherein the flexible support layer has an adhesive layer on the side from which the support member extends, and wherein the pressure exerting support member comprises two substantially planar surfaces, a first surface being attached to the flexible support layer and a second surface extending from the first surface at an angle away from the flexible support layer;

wherein the two surfaces are oriented at an acute angle.

2. The pressure wound dressing of claim 1, further comprising a removable liner on the adhesive layer opposite to the support layer.

3. The pressure wound dressing of claim 1, wherein the support layer comprises of a pliant material.

4. The pressure wound dressing of claim 3, wherein the pliant material comprises a polymeric material.

5. The pressure wound dressing of claim 1, wherein the pressure exerting support member is an integral member comprising the two surfaces that are oriented at an angle with respect to each other.

6. The pressure wound dressing of claim 5, wherein the pressure exerting support member is formed of a material that can exert a force of at least about 5 oz. per square inch to return the two surfaces to their original angular position when the two surfaces are held together.

7. The pressure wound dressing of claim 5, wherein the two surfaces are oriented at an acute angle.

8. The pressure wound dressing of claim 6, wherein the material forming the pressure exerting support member is a polycarbonate.

9. The pressure wound dressing of claim 2, wherein the removable liner comprises two adjacent pieces, each piece extending substantially to one side of the pressure exerting support member.

10. The pressure wound dressing of claim 9, wherein the adjacent pieces are a polymeric material that releases from the adhesive layer.

11. The pressure wound dressing of claim 1, further comprising a layer of a hemostatic material on the pressure exerting support member.

12. The pressure wound dressing of claim 1, further comprising a layer of collagen material on the pressure exerting support member.

13. A pressure wound dressing comprising a flexible support layer, a pressure exerting support member attached to and extending from one side of the flexible support layer, and a layer of pliant absorbent material attached to the pressure exerting support member, wherein the flexible support layer has an adhesive layer on the side from which the support member extends, and wherein the pressure exerting support member comprises two substantially planar surfaces, a first surface being attached to the flexible support layer and a second surface extending from the first surface at an angle away from the flexible support layer;

wherein the two surfaces are oriented at an acute angle.

14. The pressure wound dressing of claim 13, further comprising a removable liner on the adhesive layer opposite to the support layer.

15. The pressure wound dressing of claim 13, wherein the support layer comprises of a pliant material.

16. The pressure wound dressing of claim 15, wherein the pliant material comprises a polymeric material.

17. The pressure wound dressing of claim 13, wherein the pressure exerting support member is an integral member comprising the two surfaces that are oriented at an angle with respect to each other.

18. The pressure wound dressing of claim 17, wherein the pressure exerting support member is formed of a material that can exert a force of at least about 5 oz. per square inch to return the two surfaces to their original angular position when the two surfaces are held together.

19. The pressure wound dressing of claim 18, wherein the material forming the pressure exerting support member is a polycarbonate.

20. The pressure wound dressing of claim 17, wherein the two surfaces are oriented at an acute angle.

21. The pressure wound dressing of claim 13, wherein the pliant absorbent material comprises an open cell polyurethane foam.

22. The pressure wound dressing of claim 21, further comprising a layer of a hemostatic material on the pliant absorbent material.

23. The pressure wound dressing of claim 21, further comprising a layer of collagen material on the pliant absorbent material.

24. The pressure wound dressing of claim 14, wherein the removable liner comprises two adjacent pieces, each piece extending substantially to one side of the pressure exerting support member.

25. The pressure wound dressing of claim 24, wherein the adjacent pieces are a polymeric material that releases from the adhesive layer.

26. The pressure wound dressing of claim 13, wherein the adhesive layer contains an antibacterial agent.

27. The pressure wound dressing of claim 13, wherein the adhesive layer contains an antifungal agent.

28. A sterile wrapped pressure wound dressing, the pressure wound dressing comprising a flexible support layer, a pressure exerting support member attached to and extending from one side of the flexible support layer, and a layer of pliant absorbent material attached to the pressure exerting support member, wherein the flexible support layer has an adhesive layer on the side from which the support member extends and a removable liner on the adhesive layer opposite to the support layer, and wherein the pressure exerting support member comprises two substantially planar surfaces, a first surface being attached to the flexible support layer and a second surface extending from the first surface at an angle away from the flexible support layers;

wherein the two surfaces are oriented at an acute angle.

29. The sterile wrapped pressure wound dressing of claim 28, wherein the pressure exerting support member is an integral member comprising the two surfaces that are oriented at an angle with respect to each other.

30. The sterile wrapped pressure wound dressing of claim 29, wherein the material from which the pressure exerting support member is formed can exert a force of at least about 5 oz. per square inch to return the two surfaces to their original angular position when the two surfaces are held together.

31. The sterile wrapped pressure wound dressing of claim 30, wherein the material from which the pressure exerting support member is formed is a polycarbonate.

32. The sterile wrapped pressure wound dressing of claim 28, wherein the pliant absorbent material comprises an open cell polyurethane foam.

* * * * *